US008793209B2

(12) United States Patent
Miller, III (10) Patent No.: US 8,793,209 B2
(45) Date of Patent: Jul. 29, 2014

(54) REFLECTING THE QUANTITATIVE IMPACT OF ORDINAL INDICATORS

(76) Inventor: James R. Miller, III, Surprise, AZ (US)

( * ) Notice: Subject to any disclaimer, the term of this patent is extended or adjusted under 35 U.S.C. 154(b) by 485 days.

(21) Appl. No.: 13/166,752

(22) Filed: Jun. 22, 2011

(65) Prior Publication Data

US 2012/0330879 A1 Dec. 27, 2012

(51) Int. Cl.
*G06F 9/44* (2006.01)
*G06N 7/02* (2006.01)
*G06F 19/00* (2011.01)

(52) U.S. Cl.
CPC .................................. *G06F 19/3431* (2013.01)
USPC .......................................................... 706/52

(58) Field of Classification Search
None
See application file for complete search history.

(56) References Cited

U.S. PATENT DOCUMENTS

| | | | |
|---|---|---|---|
| 6,004,267 A | 12/1999 | Tewari et al. |
| 6,247,004 B1 | 6/2001 | Moukheibir |
| 6,375,614 B1 | 4/2002 | Braun et al. |
| 6,520,910 B1 | 2/2003 | Kohls |
| 6,754,655 B1 | 6/2004 | Segal |
| 7,908,231 B2 | 3/2011 | Miller |
| 2003/0207278 A1 | 11/2003 | Khan et al. |
| 2003/0219715 A1 | 11/2003 | Lam et al. |
| 2005/0149268 A1 | 7/2005 | Sharp |
| 2005/0209785 A1 | 9/2005 | Wells et al. |
| 2005/0262031 A1 | 11/2005 | Saidi et al. |
| 2005/0282199 A1 | 12/2005 | Slawin et al. |
| 2006/0135855 A1 | 6/2006 | Alsafadi et al. |
| 2006/0195269 A1 | 8/2006 | Yeatman et al. |
| 2006/0241923 A1* | 10/2006 | Xu et al. ............................ 703/2 |
| 2006/0289020 A1 | 12/2006 | Tabak et al. |
| 2007/0009970 A1 | 1/2007 | Heller et al. |
| 2011/0066005 A1* | 3/2011 | Rotenberg ..................... 600/301 |

FOREIGN PATENT DOCUMENTS

| | | |
|---|---|---|
| JP | 05277119 | 10/1993 |
| JP | 2004185547 | 7/2004 |

OTHER PUBLICATIONS

Norušis "Ordinal Regression", Chapter 4, PASW Statistics 18.0 Advanced Statistical Procedures Companion, Mar. 2010, pp. 69-89.*
Medcalc (Jan. 2011, p. 5), http://www.medcalc.org/manual/logistic_regression.php.*
Tibshirani "Regression Shrinkage and Selection via the Lasso", J. R. Statist. Soc. 8 (1996) 58,No. I,pp. 267-288.*
Yohannes et al. "Classification and Regression Trees: An Introduction", Technical Guide #3, IFPRI, 1999, pp. 1-29.

* cited by examiner

*Primary Examiner* — Li-Wu Chang
(74) *Attorney, Agent, or Firm* — Greenberg Traurig LLP (57) ABSTRACT

Embodiments of the invention may help improve the accuracy of individually tailored prognoses in dealing with individual patient prognoses for cancer, diabetes, multiple sclerosis, heart disease, and/or other diseases. Alternate embodiments of the invention may be useful in improving the accuracy of predictions in a variety of other contexts and fields. A method according to various embodiments of the invention includes generating a univariate impact reflecting index (UIRI) based on an indicator, the indicator having a monotonic relationship to a focal conclusion; and determining a probability that the focal conclusion will occur, wherein determining the probability is based at least partially on a regression analysis of the UIRI.

21 Claims, 3 Drawing Sheets

REFLECTING THE QUANTITATIVE IMPACT OF ORDINAL INDICATORS

DESCRIPTION OF THE INVENTION

1. Field of the Invention

Embodiments of the invention relate to systems and methods for reflecting the quantitative impact of ordinal indicators.

2. Background of the Invention

In a variety of fields and situations, it is useful to draw a conclusion based on a set of empirical data. There are many situations in science, engineering, medicine, and other fields where it is desirable to conclude which of a set of possible conditions or states exist, or predict which of a set of possible events will occur in the future. For example, it may be advantageous to be able to analyze a set of data from one or more patients in order to diagnose whether any of them has a particular disease, or to analyze data to determine which patients are likely to develop a disease in the future.

Conventional predictive methods may not be adequate to accurately make predictions in all cases. For example, in the field of medicine, research often fails to make any statements about any particular patient, instead generating conclusions about the prognostic factors generalizable to some pre-specified target population of patients.

Furthermore, conventional research conclusions based on isolated or otherwise limited samples (e.g., on patients drawn from a single institution) are frequently criticized as "biased", "unrepresentative", or "not population-based" because they are believed not to be representative of a broader patient population. Additionally, conventional research conclusions are often presented as attributes of the prognostic factors rather than as attributes of individual patients. That is, they are often displayed and organized factor-by-factor, not patient-by-patient, and describe the factors themselves, but say nothing about individual patients.

Embodiments of the invention address these and other issues.

BRIEF SUMMARY OF THE INVENTION

Embodiments of the invention may help improve the accuracy of individually tailored prognoses in dealing with individual patient prognoses for cancer, diabetes, multiple sclerosis, heart disease, and/or other diseases. Alternate embodiments of the invention may be useful in improving the accuracy of predictions in a variety of other contexts and fields.

A method according to various embodiments of the invention includes generating a univariate impact reflecting index (UIRI) based on an indicator, the indicator having a monotonic relationship to a focal conclusion; and determining a probability that the focal conclusion will occur, wherein determining the probability is based at least partially on a regression analysis of the UIRI.

A computer-readable medium according to various embodiments includes computer-executable instructions for performing a method, the method comprising: generating a univariate impact reflecting index (UIRI) based on an indicator, the indicator having a monotonic relationship to a focal conclusion; and determining a probability that the focal conclusion will occur, wherein determining the probability is based at least partially on a regression analysis of the UIRI.

A system according to various embodiments comprises a processor and a memory coupled to the processor and storing instructions executable by the processor for: generating a univariate impact reflecting index (UIRI) based on an indicator, the indicator having a monotonic relationship to a focal conclusion; and determining a probability that the focal conclusion will occur, wherein determining the probability is based at least partially on a regression analysis of the UIRI.

It is to be understood that both the foregoing general description and the following detailed description are exemplary and explanatory only and are not restrictive of the invention, as claimed.

BRIEF DESCRIPTION OF THE DRAWINGS

A more complete understanding of the present invention may be derived by referring to the detailed description and claims when considered in connection with the following illustrative figures.

DETAILED DESCRIPTION OF EXEMPLARY EMBODIMENTS

Many conventional predictive methods attempt to establish relationships between prognostic factors and focal conclusions. In the medical field, for example, data drawn from individual patients are used to draw conclusions about prognostic factors. This is a factor-centered activity, since the conclusions are about the factors. Individual patient data merely serves as a basis for drawing such conclusions. Individual patients are freely added to or removed from the effective sample as a matter of analytical convenience—according to their role in contributing to appropriate conclusions about the factors. A patient who is not from the pre-specified population or who possesses missing values on one or more prognostic factors is frequently deleted from the analysis.

In an embodiment of the invention directed to improving the accuracy of a disease prognosis, by contrast, a specific conclusion about an individual patient is sought with prognostic factors providing the data source. This is a patient-centered activity, since the conclusions are about each separate patient. In this embodiment, particular factors may be added to, removed from, and/or otherwise specially treated by the prognostic algorithm as a matter of analytical convenience according to their role in contributing to accurate predictions about individual patients. Advantageously, embodiments of the invention may still utilize data from patients even where some data are missing. Conventional methods, by contrast, often completely ignore (Le., draw no conclusion about) patients because of missing data.

Embodiments of the present invention may be applied to any situation and context to improve the accuracy of a prediction about a focal conclusion. A focal conclusion may refer to any state, event, and/or situation (e.g., patient outcome or interesting endpoint) as the focus of prognostic attention. Embodiments of the invention may be utilized to great effect in a variety of fields. For example, a patient-centered methodology according to one embodiment of the invention was applied to two different cancers, namely a sample of 1,222 melanoma patients and to a completely distinct sample of 1,225 invasive breast cancer patients. In these embodiments, for both cancers, the methodology was designed to predict the same focal event (disease-specific death within five years following initial diagnosis). These embodiments of the invention improved the correct prediction rate from 79% to 84% for melanoma, and improved the rate from 69% to 84% for breast cancer.

When the focal event is defined as the outcome of some test procedure with either a positive or a negative result, the prediction is binary. Thus, a sentinel lymph node biopsy performed on either a melanoma or a breast cancer patient may be either positive, indicating that the cancer has already penetrated the lymphatic system, or negative, providing no evidence of any such penetration, to date. In another example, when the focal event is defined as local, regional, or distant metastasis within a specified interval of time following initial diagnosis, the prediction is also binary (e.g., a patient may either survive for five years or ten years without experiencing such an event or not survive that long, event-free). In yet another example, when the length of the time interval following initial diagnosis required for a focal event to occur is being predicted, the prediction is not binary. It is a continuous, non-negative magnitude. When an event-free survival time following either initial diagnosis or some specified treatment is being predicted, the prediction is also not binary. It, too, is a continuous, non-negative magnitude.

How a focal conclusion is defined can influence the type of prognostic analysis that may be performed. For example, logistic regression is a popular and statistically powerful analysis technique for making binary (one of two mutually exclusive) predictions, while Kaplan-Meter analysis and Cox regression (proportional hazards assumed) are often utilized in predicting the likely duration of survival times. Embodiments of the invention may be utilized in conjunction with any other suitable form of regression analysis, including simple and multiple linear regression analyses.

If more than one focal event is to be predicted, at least partially and sometimes completely separate analyses may be used to support the prediction of each separate focal event. For example, it may be desirable to make predictions on multiple focal events because of differences in the nature of the desired prediction (e.g., binary event versus magnitude of elapsed time interval). Multiple focal events may also be used where the same prognostic factors are related differently to different focal events (e.g., the same genes may play different roles in mediating local, regional, and distant metastasis).

Figure 1:
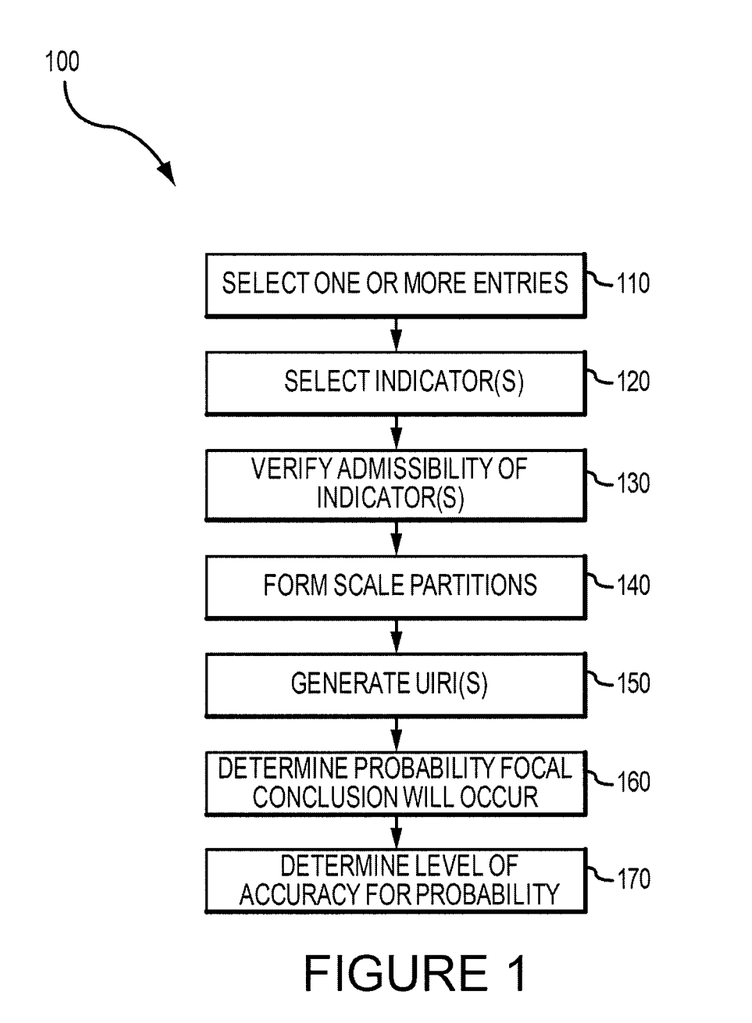
FIG. 1 is a flow diagram depicting an exemplary process according to various aspects of the present invention.

FIG. 1 depicts an exemplary method according to various embodiments of the invention. Some or all of the steps of the exemplary method in FIG. 1 may be performed in any suitable order. In the exemplary method 100, one or more entities are selected for which there are measured data (110), and one or more indicators to be used in making the prediction about the focal conclusion are selected (120). The admissibility of each selected indicator is verified (130) and scale partitions are formed (140). A univariate impact reflecting index (UIRI) is generated (150) and a probability that the focal conclusion will occur is determined based (at least partially) on a regression analysis of the UIRI (160). The exemplary method 100 further includes determining a level of accuracy for the determined probability (170).

Select Entities 110

In accordance with embodiments of the invention any number and type of different entities may be selected for any desired purpose. For example, when embodiments of the invention are applied in the medical field, the selected entities may include a group of patients similar to the targeted individual entity (e.g., patient being diagnosed) in certain respects that are relevant to predicting the chosen focal state, event, or situation. Embodiments of the invention can be particularly effective when applied to a patient-centered methodology, which focuses on a particular patient whose focal event is to be predicted on the basis of selective prognostic factors. Conventional (i.e., factor-centered) methods, by contrast, tend to focus on a pre-specified population of widespread interest to which conclusions about the prognostic factors will be generalized, based on selective patient data.

In one embodiment operating in the context of a patient-centered diagnosis, selected entities include a population of patients that are "similar" to the targeted individual patient in ways that either succeeds or fails to succeed in being prognostically useful. To be useful, an appropriate segment or stratum of the totality of all patients is similar enough to the targeted patient so that whatever happens to patients in that segment or stratum can reasonably be expected also to happen to the targeted patient. As described in more detail below in the "SELECT INDICATORS" section, measured data relevant to making the focal prediction can then be gathered for one or more of the selected entities. Entities may be selected according to any other desired criteria as well.

In one exemplary embodiment, where the entities to be selected from are groups of cancer patients, the total population of available cancer patients may be reviewed to determine whether it is homogeneous or heterogeneous. In some cases, such populations may appear to be heterogeneous in many prognostic respects, but with identifiable pockets of homogeneity. For example, focal conclusions that may be predicted with regards to the cancer patient may include, for example, relapse, recurrence, distant metastasis, and/or death. These particular events occur at successive stages of cancer progression. Consequently, stratifying or segmenting any given patient population in terms of successive stages of disease progression may produce analytically useful groups of patients that are homogenous in terms of the cause and effect relationships linking indicators to events.

In this example, the population of patients may be analyzed to stratify the patients according to their risk stage (i.e., stage of disease progression) at diagnosis and to condition, separately, all subsequent analysis procedures accordingly. Analyses may be performed separately and independently by risk category and their results merged at the end of the analysis.

In particular, an AJCC staging classification for melanoma patients, and data on the T, N, and M scales for breast cancer patients, may be used as a stratifying factor that permits separate and independent multivariate statistical analyses to be performed on all the other prognostic factors. The separate analytical results obtained for each risk group can then be merged so that a separate conclusion can be drawn about each patient. In one application of an embodiment of the invention, stratification by risk group helped improve predictive accuracy in both a sample of 1,222 melanoma patients and a sample of 1,225 breast cancer patients.

Select Indicators 120

Exemplary method 100 includes selecting one or more indicators (120) for use in predicting a focal conclusion (I.e., any conclusion of particular interest). Indicators may also be referred to herein as "prognostic factors" or "factors," while focal conclusions may also be referred to herein as "focal events." In the medical field, prognosis of disease typically spans the time interval between either a patient's initial diagnosis or some specified treatment and one of these subsequent events. Whatever is selected as the outcome or endpoint of interest can be defined as the focal event or conclusion. Predicting the occurrence of the selected event then becomes the focus of the prognostic effort.

An indicator may relate to any form of measurable evidence in any manner. An indicator may be derived directly from an observable phenomenon, or may be inferred indirectly from such an observation. For example, a conclusion that a patient has a particular disease may be inferred based one or more indicator symptoms directly observed in the patient. Alternatively, a conclusion that a subject who has just suffered a first heart attack will suffer another one within the next five years may be forecast indirectly on the basis of various indicators such as the subject's family history, medical record, diet, and the like.

Indicators and the conclusions to which they relate may apply to any desired situation, event, field of study, state, condition, and/or the like. For example, In addition to the diagnosis and prediction of disease or other medical conditions, the present invention may be used in conjunction with a variety of financial situations, such as a conclusion as to whether or not a loan will be repaid based on indicators derived from the debtor's loan application.

An indicator can include anything related to the measurement and/or observation of any type of empirical phenomenon from the selected entity or entities. An indicator may be of any form, such as: a numeric or non-numeric value; a mathematical function; any type of statement regarding a condition, event, result, state of being, etc. Indicators may be valued using any suitable measurement scale, such as a rating or scoring system, a form of categorization, and/or the like. For example, an indicator may include measurement values on a numeric scale, such as the size of a skin lesion as an indicator of skin cancer. Indicators may be based upon measured data from one or more entities (e.g., patients other than the one being diagnosed) stratified into separate respective samples (e.g., risk groups).

An indicator may also include measurement values on a non-numeric scale, such as an indicator of academic success for a student classified as "pass" or "fail" or a conditional statement classified as "true" or "false." Indicators may also be valued using any combination of numeric and non-numeric measurement scales. Where the indicator is not originally in an ordinal scale, all that is required is that the indicator is capable of being expressed in an ordinal scale.

As described previously, embodiments of the invention may utilize any suitable prognostic factors useful in predicting a focal conclusion. For example, factors that may be selected as useful in predicting the progress of melanoma may include one or more of: the age of the patient at the time of initial diagnosis (whole number of years as of most recent birthday—risk increases with age); the sex of patient (male or female—males being at higher risk); the anatomical location of the primary tumor (axial, if on head, neck, or trunk; peripheral, if on arms or legs—axial being a higher risk); the thickness of primary tumor (Breslow depth in millimeters—risk increases with thickness); Clark level of tumor invasion (I, II, III, IV, or V—risk increases with Clark level); mitotic rate of primary tumor (count of mitoses observed in a high-powered microscopic field [hpf]—risk increases with mitotic rate); and ulceration of the primary tumor (present or absent— ulcerated tumors higher risk). Mention in the preceding factors of a "higher risk" is in terms of experiencing disease-specific death and means either a higher likelihood of dying from metastatic cancer within five years of initial diagnosis or a shorter anticipated time interval until experiencing that focal event.

In another embodiment, selected indicators that may be useful in predicting the progress of breast cancer may include one or more of: the age of patient at the time of initial diagnosis (whole number of years as of most recent birthday— risk increases with age); anatomical location of primary tumor within breast (central, lateral, medial, or diffuse— diffuse higher risk); size of, primary tumor along its longest dimension (in millimeters—risk increases with tumor size); mitotic rate of primary tumor (per hpf—risk increases with mitotic rate); and ulceration of primary tumor (present or absent—ulcerated tumors higher risk).

Verify Admissibility of Indicator(s) 130

In method 100, the admissibility of the indicator(s) is verified (130). The admissibility of an indicator may be determined in any suitable manner according to any criteria, and the criteria for admissibility for one of the selected indicators need not be used to verify admissibility for other indicators. In the medical field for example, many of a patient's attributes and aspects of the patient's life situation can serve as a candidate prognostic factor (indicator). However, not all candidate indicators are admissible.

Any suitable criteria may be used to determine the admissibility of an indicator. In one exemplary embodiment applied to a patient-centered methodology for diagnosing disease, such criteria includes requiring that an indicator is recorded on a raw measurement scale containing at least two distinguishable (though not necessarily numerically coded) values—otherwise, the indicator is deemed as unable to discriminate among patients in terms of the focal event. In this exemplary embodiment, an indicator's raw scale values are further required to fall in a unique order (i.e., the indicator has an ordinal scale) that embodies increasing or decreasing degrees of whatever attribute or aspect is being measured— otherwise, the indicator is deemed to not constitute at least an ordinal measure of that raw attribute or aspect.

Admissibility of an indicator for embodiments applied to patient-centered methodologies (or other fields) may be determined based on any other criteria. For example, an indicator may be selected based on a verification that the indicator has a monotonic relationship to the focal conclusion. In other words, the indicator/factor may be required to be systematically related (either causally or correlationally) to the focal event—otherwise, it may be deemed to not have any relevant prognostic impact. The relationship of the indicator to the focal conclusion may also be required to be monotonic throughout the entire scale of values for the indicator, otherwise, the impact of the indicator on the focal event may be deemed not to be uniformly directional.

Furthermore, the relationship between the indicator and focal event may be required to have a reasonably well-established (e.g., in the relevant scientific literature) uniformly directional nature—otherwise, the prognostic methodology may be deemed to not be characterized as plausibly predictive (as opposed to just exploratory). In embodiments (such as the medical field), the indicator may be required to be available as raw data in a training sample of similar patients, with at least two different scale values assigned to patients in that sample—otherwise, the indicator may be deemed as being unable to estimate, statistically, a prognostic algorithm applicable to any individual patient, including the targeted patient.

Among other things, requiring candidate prognostic factors to possess a pre-established (e.g., through scientific literature) direction of impact on the focal event helps protect against statistical "over-fitting" of the prognostic algorithm generated by the analysis to the training data contained in the sample of similar patients. Such "fitted relationships" are based on factors with a pre-existing track record, and are thus less likely to capitalize on the chance associations that often arise in small and medium-sized samples.

Embodiments of the invention may also help protect against statistical "over-fitting" using the partitioning procedure described in more detail below. As will be described further, candidate prognostic factors that fail to demonstrate, uniformly, the previously established directionality among separate partitions, each containing at least a minimum admissible partition size (count of patients in the sample belonging to that partition) can be deemed-inadmissible and purged from the analysis.

Form Scale Partitions 140

The selected indicators can be used to predict whether, when, and in what ways a targeted entity, such as a patient, will experience a focal event. Univariate discriminability refers to the ability of any single indicator to accomplish this (i.e., acting by itself and not in some multivariate concert with other factors).

In the exemplary method 100, the raw measurement scale of each indicator for which data are available in a training sample is subdivided into partitions (140). The measurement scale of an indicator can be partitioned in any suitable manner. In one exemplary embodiment (directed to a patient-centered diagnosis for cancer), if the desired prediction is not already in binary form, a binary version of the prediction is constructed for partitioning purposes. For example, if it is stated in terms of a continuous time interval until a focal event (such as death of the patient) occurs, some standard time interval, such as five years, may be used. In this embodiment, the training sample is also divided into two separate subsamples, those patients who actually experienced the focal event (e.g., disease-specific death within five years of diagnosis) and those who experienced the complementary event (e.g., survival for more than five years).

In this exemplary embodiment, a Mann-Whitney test is performed on the two subsamples in terms of the indicator's raw measurement values. This provides an initial admissibility check on the prognostic factor's proper directionality. If higher levels of the prognostic factor are associated, historically, with a higher risk of experiencing the focal event, the subsample of patients experiencing the focal event should possess systematically higher factor values. The admissibility criterion can be strengthened by requiring some minimally acceptable value of the Mann-Whitney test's directional (one-tail) p value. Assuming initial directional admissibility, if the raw measurement scale contains only two values, or if only two distinct scale values are assigned to patients in training sample, there is only one possible way to partition the scale.

Further verification of the direction of impact (and thus the admissibility) of the indicator can be determined as follows. The indicator's sensitivity of discrimination is defined as the proportion of those patients in the sample who actually experienced the focal event (disease-specific death within five years) who also received the higher-risk raw scale value. At least one patient must actually have experienced the focal event in order to calculate any factor's sensitivity (i.e., the proportion must possess a non-zero denominator). Additionally, the factor's specificity of discrimination can be defined as the proportion of those patients in the sample who actually experienced the complementary event (survival for more than five years) who also received the lower-risk raw scale value. At least one patient must actually have experienced the complementary event in order to calculate the factor's specificity (i.e., that, proportion must likewise possess a non-zero, denominator). In this way, an indicator may be selected based on a desired sensitivity and/or specificity.

In this example, to be admissible, the factor's sensitivity (true positive proportion) must exceed the false positive proportion of patients-in-the complementary event subsample. Additionally, the factor's specificity (true negative proportion) must exceed the false negative proportion of patients in the focal event subsample. Furthermore, the conditional probability of actually experiencing the focal event, given a high-risk indication by the prognostic factor, must exceed the probability of actually experiencing the focal event, given a low-risk indication. In this exemplary embodiment, an indicator not further verified in this manner is inadmissible as it is deemed either to point in no direction or to point in the wrong direction.

In this exemplary embodiment, for indicators for which directionally is verified, and when each of the two scale values is assigned to a large enough subsample of patients, no further steps need be executed. These two values constitute the optimally partitioned scale for this prognostic factor.

Otherwise, subsequent steps are performed to partition the factor's at-least-three-valued raw measurement scale. In particular, all possible cut points within the sample of rank-ordered raw data values are checked for admissibility. If the factor's raw measurement scale contains N ordered scale values, there are N−1 potential cut points between adjacent pairs of values. An admissible cut point is one that both subdivides the sample of patients into two subsamples (each containing at least a minimum admissible partition size) and preserves the proper direction of impact in the three required senses described above.

If there is at least one admissible cut point, the optimal cut point is the one among them that maximizes the mean of the sensitivity and specificity of discrimination it provides. If the context of the analysis is such that achieving either sensitivity or specificity of discrimination is deemed more important that the other, an appropriately weighted mean can be maximized, instead. In either case, if the maximum is not unique, the admissible cut point is selected that has the largest (weighted) mean sensitivity and specificity whose minimum-sized partition is largest.

In the absence of any admissible cut points, there is no optimum cut point, and the factor scale is not partitioned. The factor is inadmissible. To illustrate, assume that higher raw data values are associated with disease-specific death within five years of diagnosis. Disease-specific death is tentatively predicted for all patients in the training sample possessing raw data values higher in the rank order than any given cut point. More than five-year survival is predicted for all patients possessing lower raw data values. The sensitivity, specificity, and partition sizes associated with that cut point can then be computed by inspecting a two-by-two cross-tabulated frequency table defined by the cut point.

The raw measurement scale is partitioned into two subscales by the optimally discriminating cut point, assuming one is successfully identified. There is a higher subscale and a lower subscale. The total sample of patients is partitioned into higher and lower subsamples, accordingly. The preceding steps are then repeated, first for each higher subscale and its associated higher subsample, and then for each lower subscale and its associated lower subsample. Successive repetitions may continue, as long as optimum cut points, optimum sub-cut points, optimum sub-sub-cut points, and so forth, continue to be identified.

At each juncture where the repeated procedure generates either a higher or a lower subscale or both, and when either or both subscales are subsequently partitioned, additional directionality checks are also performed across partitions. Failure to pass such an additional check serves to invalidate the corresponding subsequent partitioning. A candidate prognostic factor may be eliminated as inadmissible either because it points in no direction, it points in the wrong direction, or because it fails to generate at least two partitions, each one of sufficiently large subsample size. In this manner, a determination is made, based on the cut point(s) whether each scale partition has a monotonic relationship to the focal conclusion.

The maximum number of partitions that can be produced by this procedure is the number of distinguishable values in the raw measurement scale. This occurs when each scale value occupies its own separate partition. In practice, however, many prognostic factors (particularly those for predicting cancer) may only require four or fewer separate impact-reflecting scale partitions. While many such factors possess more than four values in their raw measurement scales (e.g., continuous scales measuring tumor size in millimeters), their effective discriminating power may require no more than four.

Generate UIRI 150

Among other things, generation of univariate impact-reflecting index (UIRI) values (150) produces an appropriate "spacing" among raw prognostic subscales of selected indicators. UIRI values are coded as non-negative numbers and are calculated to reflect the relative magnitudes of impact (possibly correlational) linking each factor subscale to the focal event.

As described above, the formation of scale partitions (140) generates optimal cut points that partition each admissible indicator scale into multiple subscales. Each subscale is associated with a subsample containing at least a minimum number of entities. Successive subscales are uniformly directional in their impact on the focal event. For example, in an exemplary embodiment directed to patient-centered diagnosis of death from cancer, falling into one of the multiple ordered subscales indicates monotonically greater (or lesser) probability that the focal event will occur or monotonically shorter (or longer) time intervals until the focal event occurs or monotonically shorter (or longer) survival times. As such, whereas step 140 produces a proper ordering of indicator impacts, generation of the UIRI "spaces" successive subscales according to their relative magnitudes of impact.

In the medical field, an appropriate predictive measure may include the probability that each individual patient will experience the focal event. A reasonable estimate of the probability that any randomly selected patient whose raw prognostic factor value falls into a particular subscale will experience the focal event is the proportion of such patients in the corresponding training subsample who actually do experience it.

UIRI values are observed subsample relative frequencies. Thus, if one patient's raw factor value falls within a factor subscale whose associated relative frequency is some number of percentage units greater than some other patient's associated relative frequency, a proportionately larger impact on probability of occurrence of the focal event is inferred. Similar inferences apply to other magnitudes of impact. UIRI values may be generated in any other suitable manner, such as via logistic regression. For example, zero-one dummy variables may be defined for the subscales produced in step 140. The logistic regression coefficients estimated for these dummy variables are transformed (e.g., via the predictive algorithm described below) into individual patient probabilities of experiencing the focal event. These probabilities are numerically identical to the UIRI values assigned to each patient in the training sample. As described further below, zero-one dummy variables can be also be constructed in this manner for Cox regression.

Embodiments of the invention can take into account missing or unavailable observations in any suitable manner, such as an entity that includes measured data for one or more indicators, but does not have measured data for another indicator. In one example, all such observations on any predictive factor are collected in a single, additional subscale. All patients possessing these missing observations are collected into a corresponding additional training subsample. Just as with non-missing observations, a subscale of at least the minimum partition size is verified. An estimate of the probability that any randomly selected patient whose raw prognostic factor value falls into the missing subscale will experience the focal event is the proportion of such patients in the corresponding training subsample who actually do experience it.

Adding additional subscales and corresponding training subsamples to account for missing observations in this manner may assume that no systematically different reasons for being missing are known. It is analogous to assuming that no systematically different reasons are known for producing censored observations in Kaplan-Meier and Cox regression analyses. A too-sparsely-populated missing observation subsample (and subscale) can also be combined in a non-biasing manner with a non-missing subsample (and subscale) contiguous in terms of observed focal event relative frequency.

Preferably, cut points that partition a raw factor scale into subscales associated with subsamples with too few entities are avoided. Otherwise, relative frequencies used to calculate impact-reflecting index values may provide statistically unstable spacing (relative magnitude) estimates.

Application of the exemplary embodiments in this disclosure may be applied to training samples containing any number of entities. For example, embodiments directed to patient-centered disease diagnosis may utilize tens-of-thousands of patients (or more), in which case a minimum subscale partition size might be in the hundreds or thousands of patients.

In one embodiment, zero-one dummy variables are defined (as described below) and used as independent variables in a Cox regression analysis. In this embodiment, the number (N) of raw measurement scale partitions (subscales) produced in step 140 are counted. The count includes an extra partition for missing, observations, if any exist. In the absence of missing observations, a-zero-one dummy variable is defined for each of the scale partitions, excluding the lowest-valued partition. For each of the N−1 partition-related dummy variables, a value of 1 is assigned to a patient in the total training sample if that patient's raw factor value falls in the associated partition (factor subscale). Otherwise, the partition-related dummy variable is assigned a value of 0 for that patient.

In this embodiment, all patients in the subsample associated with the lowest-valued partition will be assigned 0 values on all N−1 dummy variables. All other patients will be assigned a value of 1 on exactly one of the N−1 dummy variables and a value of 0 on all other dummy variables. If an extra scale partition has been defined for missing observations, a zero-one dummy variable is defined for each of the N−1 non-missing scale partitions, including the lowest-valued partition. Each of the N−1 partition-related dummy variables assigns a value of 1 to a patient in the total training sample, if that patient's raw factor value falls in the associated partition (factor subscale). Otherwise, the partition-related dummy variable assigns a value of 0 to that patient (including to a patient with a missing, observation).

All patients in the subsample with a missing observation on the prognostic factor being considered will be assigned 0 values on all N−1 dummy variables. All other patients will be assigned a value of 1 on exactly one of the N−1 dummy variables and a value of 0 on all other dummy variables. Dummy variables identify to which of the N scale partitions each patient in the total training sample belongs relative to the prognostic factor currently being considered.

A Cox regression analysis is performed using the elapsed time until occurrence of the focal event (e.g., disease-specific death) as the dependent variable and the N−1 zero-one dummy variables as independent variables. A table of the Cox regression results are analyzed, the table including one row for each of the N−1 dummy variables and a column of estimated relative risks (hazard ratios).

If there are no missing observations, a relative risk (e.g., 1.0) is assigned to the lowest-valued partition (subscale) for which no dummy variable was defined. An impact-reflecting index (UIRI) value is assigned to each of the N partitions (subscales) as the natural logarithm of its relative risk. This assigns an UIRI value (e.g., 0.0 by convention) to the lowest-valued partition. Successively higher-valued Partition's will be assigned successively higher-valued UIRI numbers.

If an extra scale partition has been defined for missing observations, a relative risk is assigned (e.g., 1.0 by convention) to the missing-observation partition (subscale) for which no dummy variable was defined. The smallest relative risk is identified, and all relative risks are re-scaled by dividing each by the smallest. A UIRI value is assigned to each of the N partitions (subscales) as the natural logarithm of its re-scaled relative risk. A UIRI value (e.g., 0.0 by convention) is assigned to the lowest-valued partition and successively higher-valued UIRI numbers to higher-valued partitions. For Cox regression, UIRI values are calculated as the natural logarithms of the relative risks (hazard ratios) associated with the N partitions (subscales) of a prognostic factor.

The impact-reflecting index (UIRI) values can be weighted across the selected indicators based on each indicator's propensity to correctly predict whether the focal conclusion will occur. Applying the admissibility requirements and executing the procedures described above serve (among other things) to pre-process all raw data. When stratified by risk group, as outlined above, these pre-processing steps are repeated for each risk group, separately. The result is as many tables of UIRI numbers as there are separate risk groups. In particular, forming partitions in the indicator scale and spacing the partitions are performed separately on one or more stratified risk group samples.

Each table contains as many impact-reflecting indices as there are prognostic factors specifically admissible for the corresponding risk group. Each table may be regarded as containing prognostic factor data for a separate training sample. Separate analytical results can subsequently be merged.

After pre-processing, each UIRI value in each table reflects both the direction and the magnitude of the impact of its associated prognostic factor on the focal event. Direction and magnitude of impact are encapsulated in the numeric index values. Because there are no missing observations in any table, each patient possesses a UIRI value on each admissible prognostic factor.

Raw prognostic data may be collected on many different scales. Some of these raw measurement scales may not necessarily be numerically coded. Conveniently, however, pre-processing guarantees that all numeric UIRI values in each table are normalized. By construction, the values are all on the same numeric scale. The values may be compared through software or by visual inspection. Additionally, the relative prognostic potency of separate factors can be assessed by weighting their UIRI values.

Relative factor weights may be calculated and applied in any manner. In one exemplary embodiment, relative factor weights are calculated by analyzing a table of pre-processed UIRI values for some training sample of patients prepared to predict a binary focal event. In this example, the table contains M rows, one for each patient in the sample, and N columns, one to hold UIRI numbers for each admissible prognostic factor. There are no missing observations, so the table contains the product of M times N UIRI numbers.

Based on the table, a set of N non-negative proportional weights adding to 1.0 that reflect the relative predictive potency of the N admissible prognostic factors are identified. Once identified, the N weights can be used to construct a weighted average impact-reflecting index. If all N factors were equally potent, then each weight would be 1/N, and their weighted average would be identical to their simple, unweighted average: However, if they differ in relative potency, they should receive different weights, and their weighted average would, typically, differ from their unweighted average.

In one embodiment, tailored individual patient probability of disease-specific death within five years of initial diagnosis is the focal event, while logistic regression is used as the method of analysis. In this embodiment, weights are selected to render the weighted average of the N component individual probabilities (embodied, respectively, in the N impact-reflecting indices) as close as possible to the individual probabilities produced as output from a single multivariate logistic regression, using the N impact-reflecting indices as independent input variables and by minimizing the sum of the squared deviations.

A quadratic minimization problem based on non-negative weights and a single linear constraint (the weights must add exactly to 1.0) can thus be defined and solved using Kuhn-Tucker conditions. While the weights were calculated via least-squares in this example, the output of logistic regression can still be used to assess the accuracy of all individual patient predictions.

Figure 3:
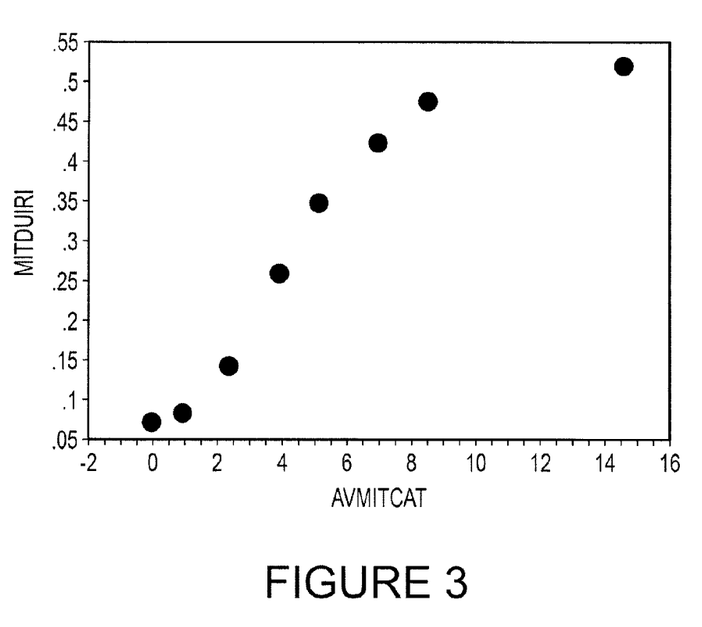
FIG. 3 is a graph showing an exemplary UIRI generated in accordance with various aspects of the invention.

FIG. 3 depicts an exemplary graph of the UIRI generated for the mitotic rate in a sample of melanoma patients. In this example, the y-axis of the UIRI graph 300 (labeled MIT-DUIRI) is the probability of disease-specific death within five years of diagnosis assigned to the sample of melanoma patients by the UIRI constructed for the mitotic rate per high-power field (HPF). Mitotic rate is partitioned (as described above) into subscales. The x-axis of the UIRI graph 300 (labeled AVMITCAT) is the mean number of mitoses per HPF of all primary tumors partitioned into each successive subscale.

Determine Probability 160

Method 100 includes determining the probability that the focal conclusion will occur (160). This probability can be determined in any suitable manner. In one embodiment, the probability that the focal conclusion will occur is determined for a single entity, namely a targeted individual patient, whose observed prognostic factor values are provided to a fitted prognostic model (I.e., into the prognostic algorithm produced by applying the appropriate statistical technique) so as to generate an individually tailored prediction of the focal state, event, or situation, and assess its accuracy.

A determination of the probability is based at least partially on a regression analysis of each UIRI generated for each indicator. Where the focal event is binary, logistic regression may be used as the principal analytical tool. The outputs of a logistic regression analysis are then modifiable to produce a tailored prediction for each entity in a sample so analyzed. In an embodiment directed to patient-centered prognosis of cancer, patients who die within five years of something else unrelated to their cancer and patients who are followed up on for no more than five years are excluded. The remaining patients either die of metastatic cancer within five years of diagnosis or survive for more than five years. In one particular example, patients were excluded from both melanoma and breast cancer samples according to these two restrictions. In each case, excluded patients accounted for between five and ten percent of those patients who otherwise qualified for inclusion.

The mathematical model underlying logistic regression assumes that the natural logarithm of the odds associated with some observable binary focal event, such as death within five years of metastatic cancer, is the following linear function of some set of K prognostic factors:

$$Y=B0+(B1)(X1)+(B2)(X2)+\ldots+(Bk)(XK), \text{ where}$$

Y, the single dependent variable, is the natural logarithm of the ratio of the probability of occurrence of the focal event (disease-specific death within five years) to the complementary probability that the event will not occur (five-year disease-specific survival); and X1, X2, ..., XK are, the K prognostic factor(s) serving as independent variables; and B0 is the "intercept" or constant-value-added regression coefficient; and B1, B2, ..., BK are the K logistic regression coefficient(s) associated, respectively, with each of the K independent variable(s); and where the values of all K independent variables and of all K+1 logistic regression coefficients are positive or negative real numbers or zero.

Once a logistic regression analysis has been performed, revised, and deemed at least minimally adequate, an estimated probability of occurrence of the focal event may be assigned to each separate patient according to the following prognostic algorithm:

$$\text{EXP }[B0+(B1)(X1)+(B2)(X2)+\ldots+(BK)(XK)]/\{1+\text{EXP }[B0+(B1)(X1)+(B2)(X2)+\ldots+(BK)(XX)]\}, \text{ where}$$

EXP means to exponentiate the immediately following bracketed expression relative to the natural logarithm base; and B0, B1, ..., BK are the numeric values of the regression coefficients estimated by the logistic analysis; and X1, X2, ..., XN are the numerically coded values of that patient's prognostic factors.

With regards to missing or inadmissible observations, the two previously described restrictions eliminated missing data on the dependent variable. Additionally, missing observations on all independent variables (prognostic factors) may be addressed as described above in step 150.

Using the above prognostic algorithm, an individually tailored prediction of the focal event can be made for every entity (patient) in the sample. The prediction is a probability that each entity experiences the focal event (e.g., disease-specific death within five years of diagnosis). These individually tailored probabilities may be used as the predictive measure in a patient-centered prognosis. The prognostic algorithm assigns such a probability to any patient, including patients not included in the logistic regression analysis, as a function of that patient's numeric values of the K prognostic factors.

Other regression analyses may be used. For example, had the focal event been defined in terms of the time interval between diagnosis and disease-specific death, analogous individually tailored probabilities could have been generated by performing a Cox regression analysis on the same K prognostic factors. The proportional hazards model underlying Cox regression assumes that the population from which the sample was obtained possesses a baseline hazard function of this elapsed time interval. Each patient's individual hazard function is assumed to be directly proportional to the shared baseline hazard function. Each patient possesses a separate proportionately factor that is independent of the elapsed time interval. It is calculated by exponentiating the following homogeneous linear function of the K prognostic factors:

$$Y=\text{EXP }[B1)(X1)+(B2)(X2)+\ldots+(BK)(XK)], \text{ where}$$

Y is a given patient's proportionality factor that is to be multiplied by the shared baseline hazard function to obtain that patient's individual hazard function, and where EXP and the B, X, and K values are defined as in logistic regression, except that B1 through BK are now Cox regression coefficients.

Associated with the baseline hazard function is a baseline survival function of the same elapsed time interval. It, too, is shared by all patients in the population. Cox repression analysis can be programmed to produce both baseline functions. The individually tailored prognostic algorithm generated from Cox regression then uses each patient's proportionality factor to exponentiate the baseline survival function. Applying this algorithm to a particular patient's prognostic factors and evaluating the resulting function at a particular elapsed time interval (five years) gives an individually tailored (five-year) survival probability. Conceptually, this is the complement of the focal event probability generated by Logistic regression from the same prognostic factors.

Determine Accuracy Of Probability 170

In method 100, the accuracy of the generated probability is determined (170). Any suitable number and type of measures for predictive accuracy may be used. For example, the individually tailored probabilities assigned by the prognostic algorithm to any set of entities may be submitted to a traditional receiver operating characteristic (ROC)/area under the ROC curve (AUC) analysis. A numeric AUC value between 0.0 and 1.0 may be estimated from any such sample. The larger the estimated AUC value, the better that prognostic algorithm may be judged as discriminating among patients in the sample in terms of whether or not each one experiences the binary focal event. An AUC value of 1.0 indicates perfect discrimination.

Another way to judge accuracy may be derived from the same set of individually tailored probabilities in what may be referred to as a maximum probability of correct prediction analysis. In this analysis, the probabilities are rank-ordered from largest to smallest and each cut point between adjacent probabilities in the rank order is tested as a possible dichotomous discriminator. Tentatively, a prediction is made that all entities whose probabilities exceed a given cut point experience the focal event, while all entities with lower probabilities do not. The correct predictions for that cut point are counted, and the cut point that offers the highest correct count is selected. The count may be defined as the maximum possible number (or percentage) of correct predictions. An AUC value of 1.0 implies a 100% correct prediction rate, and vice-versa.

Absolute probabilistic error provides another measure that may be used in conjunction with embodiments of the invention. Absolute probabilistic error is the absolute value of the difference between each patient's probability of experiencing the focal event and what actually occurs. Actual occurrence is coded as 1.0. Actual non-occurrence is coded as 0.0. The absolute difference is useful in comparing the accuracy of two or more alternative methods of generating tailored individual probabilities (i.e., via two or more alternative prognostic algorithms). In this manner, the statistical power of matched sample analysis can then be used to conclude which generation method provides more accurate probabilities.

Another method for determining the accuracy of a probability includes a probability scale characteristics analysis. Among other things, this method may be used to help overcome issues associated with individually tailored focal event probabilities not being familiar in traditional prognostic research methodology. The mean probability assigned by logistic regression to a sample of patients is numerically equal to the incidence (relative frequency) of the focal event in that sample. However, other forms of regression analysis, including Cox regression, may not guarantee the same average accuracy. By partitioning the probability scale (e.g., into quartiles), similar comparisons may be repeated between mean probabilities and actual incidences throughout the entire range of the scale.

Exemplary System

Exemplary methods according to embodiments of the present invention may be implemented in any manner, such as through a software program operating on a computer system. Such a software program may be stored on any computer-readable medium, such as floppy disks, hard disks, CD-ROMs, DVDs, any type of optical or magneti-optical disks, volatile or non-volatile memory, and/or any other type of media suitable for storing electronic instructions and capable of interfacing with a computing device.

Methods according to aspects of the present invention may operate in conjunction with any type of computer system, such as a personal computer (PC), server, cellular phone, personal digital assistant (PDA), portable computer (such as a laptop), embedded computing system, and/or any other type of computing device. The computer system may include any number of computing devices connected in any manner, such as through a distributed network. The computer system may communicate and/or interface with any number of users and/or other computing devices to send and receive any suitable information in any manner, such as via a local area network (LAN), cellular communication, radio, satellite transmission, a modem, the Internet, and/or the like.

Figure 2:
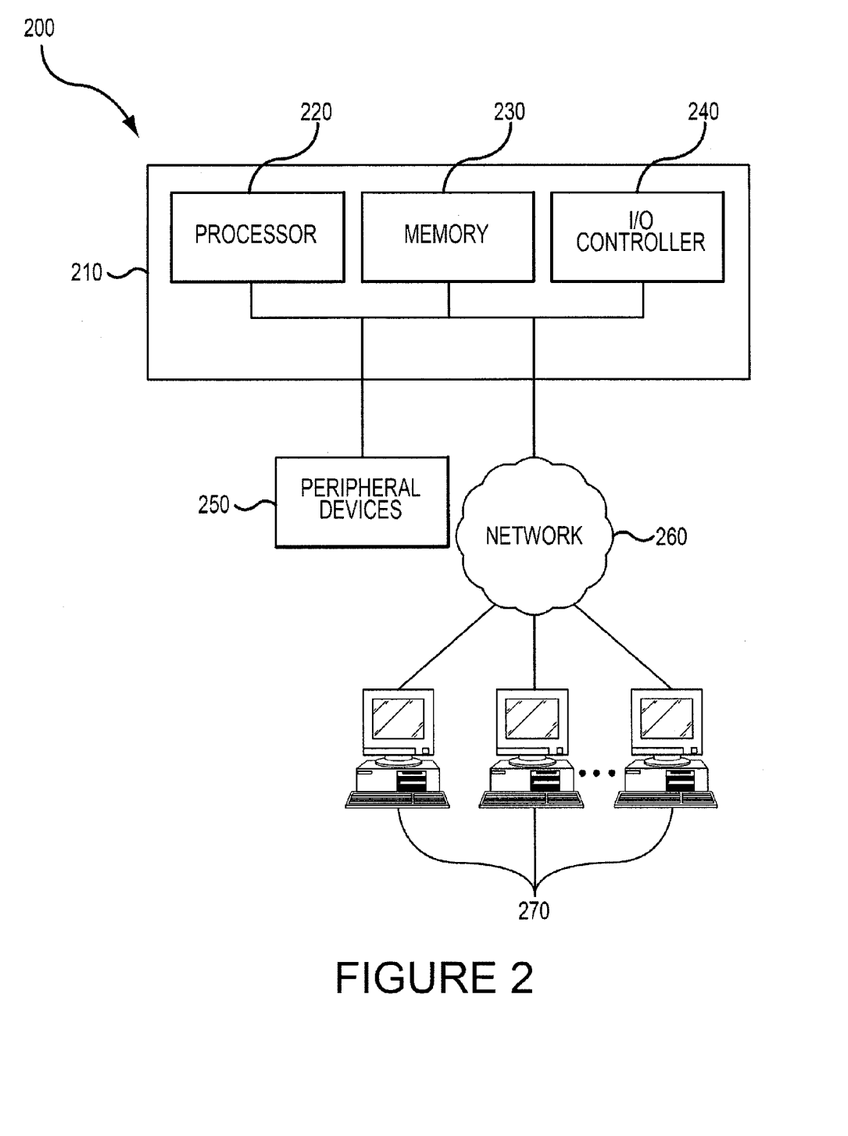
FIG. 2 is a block diagram of an exemplary system according to various aspects of the present invention.

For example, FIG. 2 depicts an embodiment of a system 200 that may be used to perform the exemplary method 100 in FIG. 1, as well as methods according to other embodiments of the invention. In this exemplary embodiment, the system 200 includes a computer system 210, which includes a processor 220, memory 230, and input/output (I/O) controller 240. The computer system 210 may communicate with one or more peripheral devices 250 as well as with one or more additional computing devices 270 through a network 260.

The computer system 210 may store a software program configured to perform methods according to embodiments of the invention in the memory 230 and run the software program using the processor 220. The computer system 210 may include any number of individual processors 220 and memories 230. Information may be provided to the computer system 210 by a user through the one or more peripheral devices 250 controlled by the I/O controller 240. Such information may also be provided from other computing devices 270 connected to the computer system 210 through a network 260. The computer system 210 may allow information to be processed by the software program and displayed to various peripheral devices 250 (such as monitors and printers). The software program may be controlled and interacted with in any manner by a user through other peripheral devices 250 (such as a mouse, keyboard, monitor, speakers, printer, external memory device, and/or any other system or device).

The particular implementations shown and described above are illustrative of the invention and its best mode and are not intended to otherwise limit the scope of the present invention in any way. Indeed, for the sake of brevity, conventional data storage, data transmission, and other functional aspects of the systems may not be described in detail. Methods illustrated in the various figures may include more, fewer, or other steps. Additionally, steps may be performed in any suitable order without departing from the scope of the invention. Furthermore, the connecting lines shown in the various figures are intended to represent exemplary functional relationships and/or physical couplings between the various elements. Many alternative or additional functional relationships or physical connections may be present in a practical system.

Changes and modifications may be made to the disclosed embodiment without departing from the scope of the present invention. These and other changes or modifications are intended to be included within the scope of the present invention, as expressed in the following claims.

What is claimed is:

1. A computer-implemented method comprising:
generating, by a computer system, a univariate impact reflecting index (UIRI) based on an indicator, the indicator having a monotonic relationship to a focal conclusion, wherein the UIRI spaces subscales of the indicator according to a magnitude of impact of the indicator to the focal conclusion; and
determining, by the computer system, a probability that the focal conclusion will occur, wherein determining the probability is based at least partially on a regression analysis of the UIRI.

2. The method of claim 1, further comprising determining a level of accuracy for the determined probability.

3. The method of claim 1, further comprising forming partitions in the scale for the indicator using one or more cut points within the scale.

4. The method of claim 3, wherein generating the univariate impact reflecting index includes spacing the partitions.

5. The method of claim 4, wherein forming partitions in the scale and spacing the partitions are performed separately on one or more stratified samples.

6. The method of claim 2, wherein determining the level of accuracy for the determined probability is based on one or more of:
a receiver operating characteristic (ROC) analysis;
an area under the ROC curve (AUC) analysis;
a maximum probability of correct prediction analysis;
an absolute probabilistic error analysis; and
a probability scale characteristics analysis.

7. The method of claim 1, wherein the probability that the focal conclusion will occur is determined for a single entity.

8. The method of claim 7, wherein the indicator is based upon measured data from one or more other entities stratified into separate respective samples.

9. The method of claim 8, further comprising selecting the one or more other entities based on one or more similarities between the single entity and the one or more other entities.

10. The method of claim 1, further comprising selecting the indicator from a plurality of possible indicators.

11. The method of claim 10, wherein selecting the indicator is at least partially based on at least one of a desired sensitivity and a desired specificity.

12. The method of claim 10, wherein selecting the indicator includes verifying that the indicator has a monotonic relationship to the focal conclusion.

13. The method of claim 10, wherein selecting the indicator includes:
determining one or more cut points for the indicator;
determining whether a partition formed by one or more of the cut points has at least a minimum scale partition size; and determining, based the one or more cut points, whether the scale partition has a monotonic relationship to the focal conclusion.

14. The method of claim 1, further comprising verifying the indicator's admissibility, where verifying the indicator's admissibility includes verifying an ordinal scale for the indicator.

15. The method of claim 14, wherein generating the UIRI is based on the verified ordinal scale for the indicator.

16. The method of claim 1, wherein the regression analysis is selected from the group consisting of:
a logistic regression analysis;
a Cox proportional hazards analysis; and
a linear regression analysis.

17. The method of claim 1, further comprising:
generating a respective UIRI for each of a plurality of indicators, wherein determining the probability is based at least partially on a regression analysis of each of the generated UIRIs.

18. The method of claim 17, further comprising weighting values of an UIRI index of an indicator of the plurality of indicators based on the indicator's propensity to correctly predict whether the focal conclusion will occur.

19. The method of claim 17, wherein each indicator of the plurality of indicators is based upon measured data from one or more other entities, and wherein at least one of the one or more entities includes measured data for a first indicator of the plurality of indicators and does not have measured data for a second indicator of the plurality of indicators.

20. A tangible, non-transitory computer-readable medium storing instructions that, when executed by a computing device, cause the computing device to:
generate a univariate impact reflecting index (UIRI) based on an indicator, the indicator having a monotonic relationship to a focal conclusion, wherein the UIRI spaces subscales of the indicator according to a magnitude of impact of the indicator to the focal conclusion; and
determine a probability that the focal conclusion will occur, wherein determining the probability is based at least partially on a regression analysis of the UIRI.

21. A system comprising:
a processor;
a memory coupled to the processor and storing instructions that, when executed by the processor, cause the system to:
generate a univariate impact reflecting index (UIRI) based on an indicator, the indicator having a monotonic relationship to a focal conclusion, wherein the UIRI spaces subscales of the indicator according to a magnitude of impact of the indicator to the focal conclusion; and
determine a probability that the focal conclusion will occur, wherein determining the probability is based at least partially on a regression analysis of the UIRI.

* * * * *